United States Patent
Sabattier et al.

(10) Patent No.: US 10,278,888 B2
(45) Date of Patent: May 7, 2019

(54) TREATMENT DEVICE WITH LIGHT GUIDE

(71) Applicant: SEB S.A., Ecully (FR)

(72) Inventors: Johan Sabattier, Mornant (FR); Franck Mandica, Francheville (FR)

(73) Assignee: SEB S.A., Ecully (FR)

( * ) Notice: Subject to any disclaimer, the term of this patent is extended or adjusted under 35 U.S.C. 154(b) by 0 days.

(21) Appl. No.: 15/761,302

(22) PCT Filed: Sep. 19, 2016

(86) PCT No.: PCT/FR2016/052368
§ 371 (c)(1),
(2) Date: Mar. 19, 2018

(87) PCT Pub. No.: WO2017/051102
PCT Pub. Date: Mar. 30, 2017

(65) Prior Publication Data
US 2018/0256439 A1 Sep. 13, 2018

(30) Foreign Application Priority Data
Sep. 21, 2015 (FR) ..................................... 15 58888

(51) Int. Cl.
*A61H 7/00* (2006.01)
*A61H 23/02* (2006.01)
(Continued)

(52) U.S. Cl.
CPC .......... *A61H 7/005* (2013.01); *A46B 15/0036* (2013.01); *A61H 15/0085* (2013.01);
(Continued)

(58) Field of Classification Search
CPC ................ A61H 7/005; A61H 23/0254; A61H 15/0085; A61H 15/02; A61H 2205/022;
(Continued)

(56) References Cited

U.S. PATENT DOCUMENTS

2003/0032900 A1* 2/2003 Ella ..................... A61H 7/008
601/6
2004/0260209 A1* 12/2004 Ella ..................... A61B 18/203
601/7
(Continued)

FOREIGN PATENT DOCUMENTS

CN       202537881 U     11/2012
EP       2 862 555 A1     4/2015
(Continued)

OTHER PUBLICATIONS

English translation for EP 2862554, espacenet.com, translated on Oct. 1, 2018.*
(Continued)

*Primary Examiner* — Rachel T Sippel
*Assistant Examiner* — Tu A Vo
(74) *Attorney, Agent, or Firm* — Pillsbury Winthrop Shaw Pittman LLP

(57) ABSTRACT

A treatment device for treating the skin, includes a body including a housing forming a gripping area, an electrical supply device arranged in the body, a treatment head including a massage device, a device for maneuvering the massage device, actuated by an electric motor connected to the electrical supply device, a light source, and a light guide having a projection surface for receiving light from the light source and for projecting a light beam towards an area on the skin. The light guide includes a face opposite the projection surface, including a distribution system for distributing the light along the projection surface, and the massage device has an area for contact with the skin to be massaged. The area transmits the light and consists of a thermoplastic elastomer (TPE) material having a light transmission of between 0.8 and 0.9 for light with a wavelength of 590 nm or 630 nm.

13 Claims, 6 Drawing Sheets

(51) Int. Cl.
*A61N 5/06* (2006.01)
*A46B 15/00* (2006.01)
*A61H 15/02* (2006.01)
*A61H 15/00* (2006.01)
*A61B 17/00* (2006.01)

(52) U.S. Cl.
CPC ......... *A61H 15/02* (2013.01); *A61H 23/0254* (2013.01); *A61N 5/0616* (2013.01); *A46B 2200/102* (2013.01); *A61B 2017/00734* (2013.01); *A61B 2017/00747* (2013.01); *A61H 2015/0064* (2013.01); *A61H 2201/0188* (2013.01); *A61H 2201/10* (2013.01); *A61H 2201/1207* (2013.01); *A61H 2201/1215* (2013.01); *A61H 2201/1472* (2013.01); *A61H 2201/1685* (2013.01); *A61H 2201/1692* (2013.01); *A61H 2201/5025* (2013.01); *A61H 2205/022* (2013.01); *A61N 2005/0644* (2013.01); *A61N 2005/0652* (2013.01); *A61N 2005/0659* (2013.01); *A61N 2005/0662* (2013.01); *A61N 2005/0666* (2013.01)

(58) Field of Classification Search
CPC .... A61H 2201/1207; A61H 2201/5025; A61H 2201/1472; A61H 2201/0188; A61H 2201/1215; A61H 2015/0064; A61H 2201/1685; A61H 2201/1692; A61H 2201/10; A46B 15/0036; A46B 2200/102; A61N 5/0616; A61N 2005/0666; A61N 2005/0662; A61N 2005/0652; A61N 2005/0644; A61N 2005/0659; A61B 2017/00734; A61B 2017/00747
See application file for complete search history.

(56) References Cited

U.S. PATENT DOCUMENTS

| | | | |
|---|---|---|---|
| 2004/0260210 A1* | 12/2004 | Ella | A61H 7/008 601/7 |
| 2004/0260212 A1* | 12/2004 | Cho | A61H 23/0218 601/15 |
| 2006/0247742 A1* | 11/2006 | Lee | A61H 7/003 607/89 |
| 2006/0253051 A1* | 11/2006 | Milne | A61H 7/001 601/15 |
| 2007/0027411 A1* | 2/2007 | Ella | A61H 7/008 601/7 |
| 2008/0014011 A1* | 1/2008 | Rossen | A45D 34/041 401/195 |
| 2008/0214968 A1* | 9/2008 | Milne | A61H 23/0263 601/15 |
| 2008/0262394 A1* | 10/2008 | Pryor | A61H 7/007 601/15 |
| 2008/0275532 A1* | 11/2008 | Yamazaki | A61N 5/0616 607/88 |
| 2009/0177125 A1 | 7/2009 | Pilcher et al. | |
| 2010/0004570 A1* | 1/2010 | Torres Martin | A61H 7/005 601/17 |
| 2012/0109041 A1* | 5/2012 | Munz | A45D 34/041 604/20 |
| 2013/0046212 A1* | 2/2013 | Nichols | A46B 7/04 601/18 |
| 2013/0131559 A1* | 5/2013 | Vandenbelt | A61N 5/0617 601/2 |
| 2013/0245515 A1* | 9/2013 | Chen | A61H 7/007 601/101 |
| 2013/0261385 A1* | 10/2013 | Zipper | A61H 19/40 600/38 |
| 2014/0135798 A1 | 5/2014 | David | |
| 2014/0142471 A1* | 5/2014 | Chambon | A61B 18/203 601/18 |
| 2014/0142472 A1* | 5/2014 | Giraud | A61H 7/005 601/18 |
| 2014/0142480 A1* | 5/2014 | Giraud | A61N 1/303 601/127 |
| 2014/0202493 A1* | 7/2014 | Zelickson | A46B 13/02 15/22.1 |
| 2015/0045702 A1* | 2/2015 | Lin | A61N 5/0616 601/19 |
| 2015/0165238 A1* | 6/2015 | Slayton | A61B 18/18 601/2 |
| 2015/0283025 A1* | 10/2015 | Ledany | A61H 23/0263 601/18 |
| 2015/0327653 A1* | 11/2015 | Decaux | A45D 34/041 604/20 |
| 2015/0360014 A1* | 12/2015 | Decaux | A61M 35/003 604/20 |

FOREIGN PATENT DOCUMENTS

| | | | |
|---|---|---|---|
| EP | 2 862 556 A1 | 4/2015 | |
| EP | 2862554 A1 * | 4/2015 | ........ A61H 15/0085 |
| KR | 20-2009-0001911 U | 2/2009 | |

OTHER PUBLICATIONS

International Search Report as issued in International Patent Application No. PCT/FR2016/052368, dated Dec. 16, 2016.
International Preliminary Report on Patentability and the Written Opinion of the International Searching Authority as issued in International Patent Application No. PCT/FR2016/052368, dated Mar. 27, 2018.

\* cited by examiner

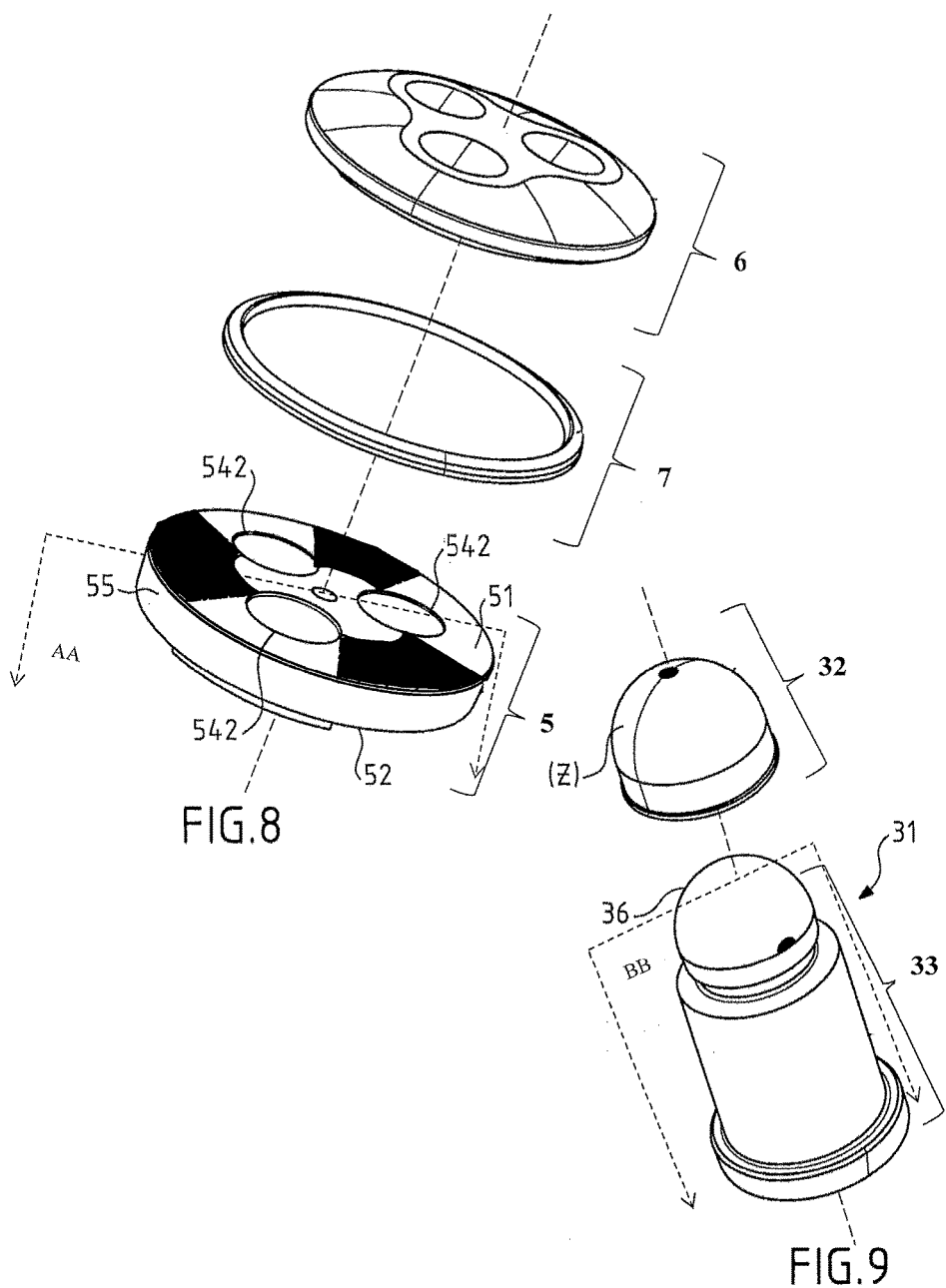

TREATMENT DEVICE WITH LIGHT GUIDE

CROSS-REFERENCE TO RELATED APPLICATIONS

This application is the U.S. National Stage of PCT/FR2016/052368, filed Sep. 19, 2016, which in turn claims priority to French patent application number 1558888 filed Sep. 21, 2015. The content of these applications are incorporated herein by reference in their entireties.

This invention concerns a skin treatment device, for treatment of the skin of the face in particular, intended to provide treatments in various forms in order to produce a brightening, recontouring, anti-aging or anti-wrinkle effect. The treatment is provided by delivery of light energy to the skin and also by a mechanical action of massaging means.

We know of a document, KR20090001911, which informs about a massage device comprising a treatment head comprising a vacuum chamber intended to vacuum the skin. The chamber includes two parallel rollers motorized in order to turn in the same direction. The device further comprises a light emitter in the bottom of the chamber behind the said rollers. The light source is a light-emitting diode, commonly called an LED, intended to project light simultaneously with the movement of the rollers. The disadvantage of such an arrangement of the light source is that it is distant from the area to be projected, that is, from the plane tangent to the outside of the rollers, which means that the intensity of the projected light is diminished. In addition, a portion of the light beams is concealed by the two rollers, which reduces the effectiveness of the light treatment.

We know of another document, CN202537881, which describes a massage device comprising a treatment head with massage heads intended to massage the skin. The heads are motorized in order to make a rotational movement. The device further comprises light sources arranged inside the treatment head in order to provide a treatment other than mechanical massage. However, this device has the disadvantage of light projection that is not powerful and especially not homogeneous, whether on the massage heads or in the area between the heads.

The goal of this invention is to remedy at least in part the aforementioned disadvantages and to propose a skin treatment device that permits providing at least one mechanical treatment combined with a light treatment on a defined area.

Another goal of the invention is a skin treatment device that is able to produce lighting at a targeted and homogeneous intensity on a defined surface.

Another goal of the invention is a skin treatment device whose light sources permit lighting at least one portion of an area in contact with the mechanical massage means with which they are associated.

Another goal of the invention is a skin treatment device with an arrangement of light sources and mechanical massage means optimized to reduce the dimensions of the device.

Yet another goal of the invention is a multipurpose skin treatment device that is easy to use and inexpensive.

These goals are achieved with a skin treatment device comprising:
- a body comprising a housing forming a gripping area,
- electrical supply means arranged in the said body,
- at least one treatment head comprising massage means,
- means for maneuvering the said massage means actuated by an electric motor which is connected to the said electrical supply means,
- at least one light source,
- at least one light guide having a projection surface intended for receiving light emitted by the said at least one light source and for projecting at least one light beam toward an area on the skin.

According to the invention, the said at least one light guide comprises a face opposite the said projection surface, the said opposite face comprising distribution means intended for distributing the light along the said projection surface, and at least one massage means has an area (Z) for contact with the skin to be massaged, the said area (Z) being intended for transmitting the light and consisting of a thermoplastic elastomer (TPE) material having a light transmission of between 0.8 and 0.9 for light with a wavelength of 590 nm or 630 nm, known for its photomodulation effects.

In this way, the light reaching the opposite face is redirected toward the projection surface. The light diffused by the projection surface is then projected toward the skin, but also toward the at least one massage means which, through the formation of its area in contact with the skin to be massaged, also transmits the light toward the skin instead of simply hiding it. This permits diffusing more light, in a homogeneous manner and as close as possible to the skin. The known effects of these lights on the skin are in particular stimulation of collagen production and more generally an improvement in the skin's appearance, to give it a younger and more uniform appearance. These effects have in particular been described in numerous publications by McDaniels and Weiss since 2004. Material with such an optical property permits better transmission of visible light as well as infrared.

Advantageously, the said material has a hardness of between 30 and 70 Shore A. This provides a sensation that is pleasant to the touch and makes the massage more effective.

In addition, the said contact area (Z) has an unpolished surface finish with an arithmetic roughness Ra of about 0.5 µm to 1 µm. Such a surface finish permits improving the uniformity of the light flow.

According to the invention, the said massage means comprise at least one massage head intended to be moved in rotation according to at least one vertical axis of rotation (A1, A2, A3) which is perpendicular to the projection surface.

Advantageously, the said massage head has a hemispheric portion. The massage head thus has a rounded end permitting a pleasant massage.

In addition, the said massage head comprises a cover defining the said contact area (Z) and the said cover is fixed to the hemispheric portion by overmolding. The said cover is thus intended to rest on the skin during treatment. The cover is manufactured independently from the massage head, such that the latter may be made of another, more rigid material in order to ensure the solidity of the device.

According to another characteristic of the invention, the said light source comprises a plurality of light-emitting diodes distributed regularly around the said light guide. This permits good lighting of the treatment area from all directions.

According to another characteristic of the invention, the said distribution means comprise at least one peripheral slope intended to reflect the light toward the periphery of the light guide. This permits good lighting of the periphery of the treatment area.

According to yet another characteristic of the invention, the said distribution means comprise at least one intermediate slope intended to reflect the light toward an intermediate area of the light guide. This permits good lighting of the area between the massage heads and the periphery.

According to yet another characteristic of the invention, the said massage head comprises reflection means permitting reflecting the light toward the said contact area (Z). This permits the light to pass through the massage head and then toward the contact area.

Advantageously, the said at least one massage head can be detached from the said body. Reversible fixing means that are within the grasp of those skilled in the art may be envisioned.

In addition, the device comprises at least two different treatment heads interchangeable on the body in order to offer users at least two different treatments in the same device.

The invention will be more fully understood in consideration of the embodiments, which are in no way restrictive, illustrated in the attached drawings, in which:

FIGS. 6 to 8 illustrate the light guide according to a second embodiment, FIG. 9 is an exploded view of a massaging means.

Figure 1:
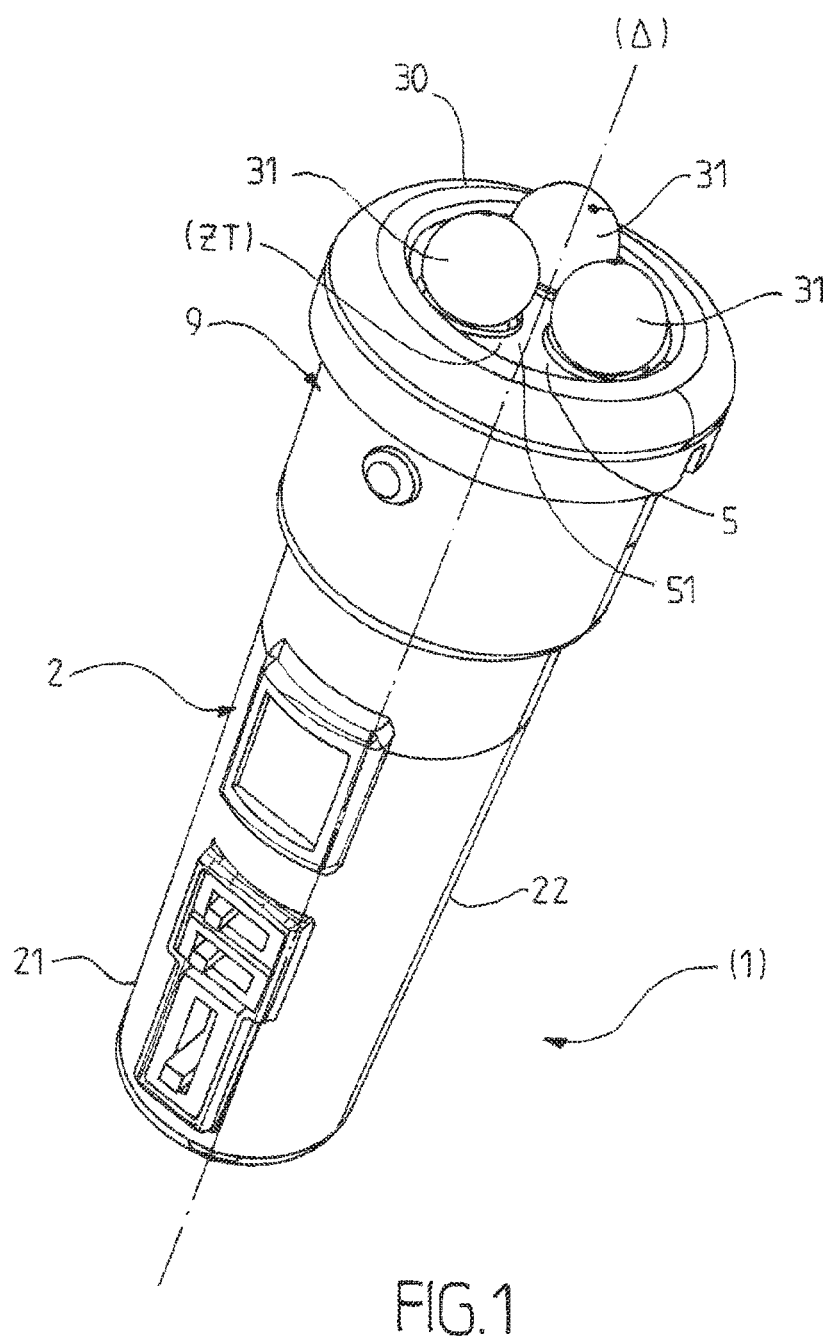
FIG. 1 is a perspective view of the device according to the invention.
Figure 2:
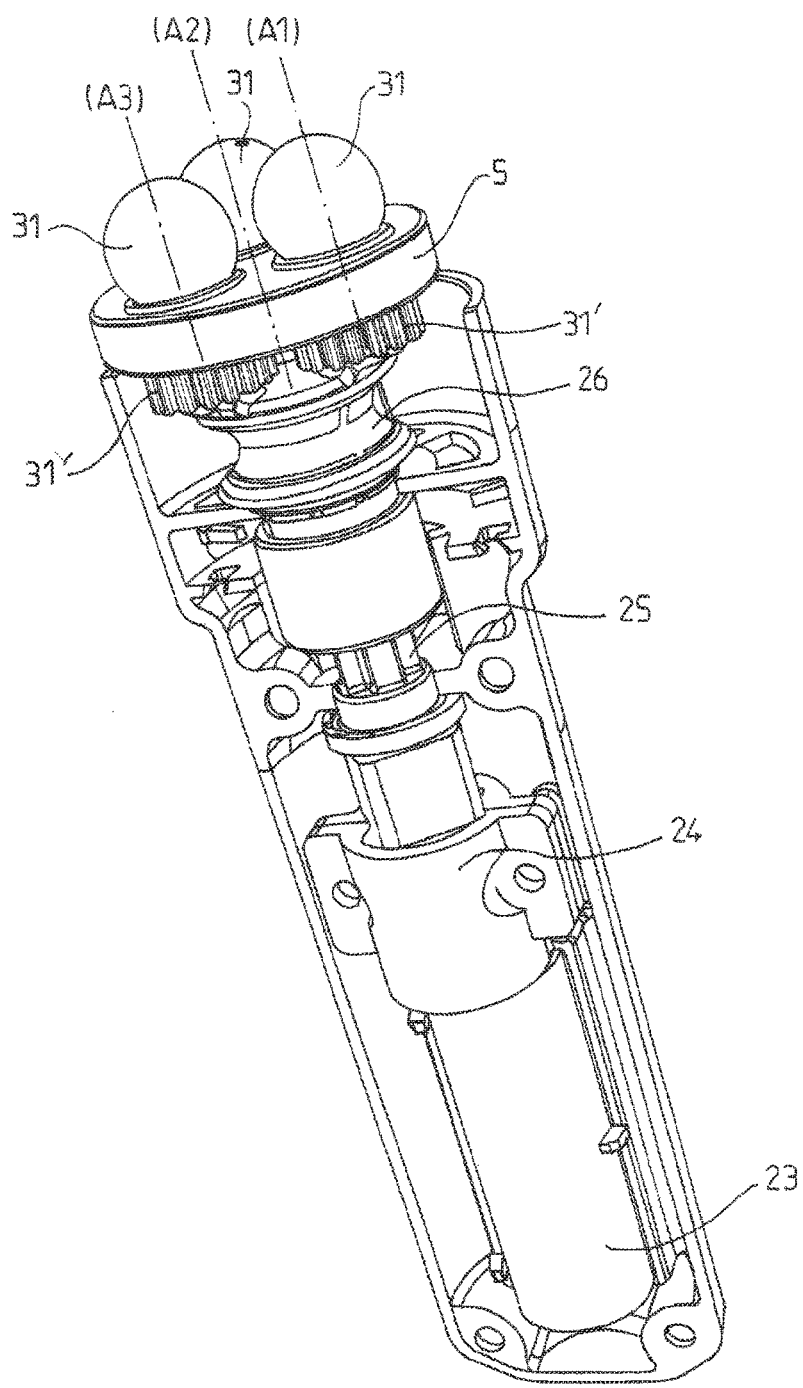
FIG. 2 is a perspective view of the interior of the device.

The skin treatment device as illustrated in FIGS. 1 and 2 and designated overall by the reference 1 comprises a treatment head 9 and a body 2. The said body 2 having a longitudinal form with a central axis (Δ) comprises a housing composed of two half-housings 21, 22 together forming a gripping area. The treatment head 9 being mounted on one of the ends of the body 2 has a treatment area (ZT) intended to function on or close to the skin. The said treatment area (ZT) is the combination of a light projection area and an area with mechanical massage means. The treatment head 9 has a substantially cylindrical shape coaxial with the body 2 of the device. The treatment head 9 comprises a bearing ring 30 delimiting the treatment area (ZT) inside which are massage means, which are three massage heads 31 projecting from the plane of the ring 30. The treatment head 9 comprises removable adaptation means on the body 2, and the said adaptation means can be formed of a sheath permitting the treatment head 9 to be partly engaged with the body 2. Thus, the device may comprise several different treatment heads to be used on the body 2 interchangeably. As visible in FIG. 2, the body 2 comprises an electric motor 24 connected to an output shaft 25 by transmission means, the output shaft 25 being accessible from the end of the adaptation means. The electric motor 24 is powered by electrical supply means, for example, a battery 23, and controlled by a control unit connected to a manual control interface accessible from outside the body 2. The manual control interface may, for example, comprise an on/off switch and/or means for manual selection of operation programs.

Figure 3:
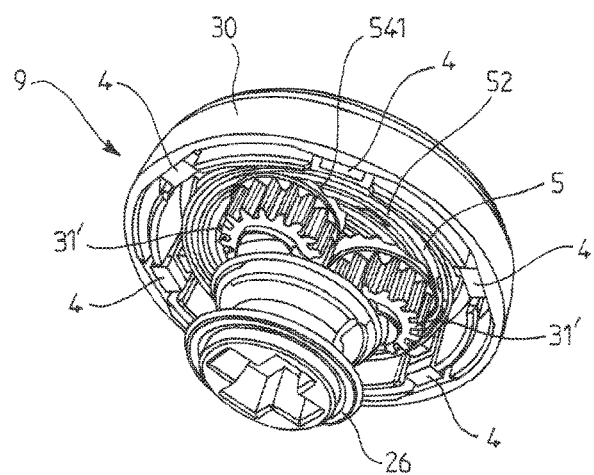
FIGS. 3 and 4 illustrate the treatment head according to the invention.
Figure 4:
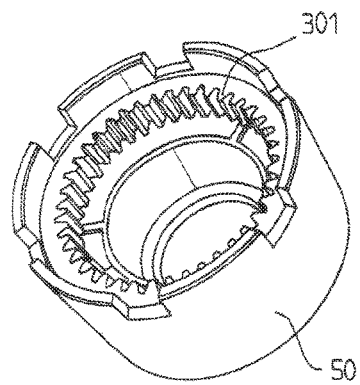

As illustrated in FIGS. 2 to 4, each massage head 31 is connected to maneuvering means 26, 31' in order to be rotated not only with respect to a central axis (Δ), but also with respect to a vertical axis of rotation A1, A2, A3 specific to it. To do this, the maneuvering means 26, 31' comprise a driver 26 intended to interlock with the output shaft 25 of the motor in order to set it moving. For example, the driver 26 may have a cross-shaped cavity intended to receive the output shaft 25 by a protuberance on the latter having the same shape. The driver 26 with axis (Δ) has on an upper face three pins (not illustrated) each engaged in an axial bore of a planetary gear 31'. Each massage head is fixed to the corresponding planetary gear. Each planetary gear meshes with the toothed periphery 301 of a fixed ring 50, illustrated in FIG. 4, such that the rotation of the driver 26 produces the planetary movement of the massage heads 31, that is, a principal rotational movement of the three heads around the central axis (Δ) combined with a secondary rotational movement of each of the heads around the vertical axis of rotation A1, A2, A3 which moves in rotation around the central axis (Δ) when the device is operating.

The treatment head 9 as presented makes it possible to knead the skin of the face, in particular the broad areas such as the cheeks or the forehead, in order to activate microcirculation and stimulate natural mechanisms for production of skin-structuring proteins, and thus prevent signs of aging. These effects are accentuated by the presence of light on the skin. For this reason, the device comprises a plurality of light sources 4 which are LEDs (light-emitting diodes) arranged inside the treatment head 9. According to the example illustrated in FIG. 7, the LEDs 4 are 24 in number and are distributed regularly around the treatment head 9. Support means 40 for the LEDs can be used, such as printed circuit boards (PCB), which are boards that integrate an electric circuit to power the LEDs mounted on top. This LED arrangement technique is known to persons skilled in the art. The PCBs are preferably white in order to optimize the emission of light toward the interior of the device. Each PCB supports two LEDs in order to have a more constant distance between each LED and the light guide. All LEDs are positioned on the same line so as to reduce the influence of the rotation of the treatment head. Preferably, 18 visible LEDs and 6 infrared LEDs are used.

In order to properly distribute the light on the treatment area (ZT), the treatment head 9 comprises in its interior a light guide 5 which has the objective of guiding, homogenizing and concentrating the light beams coming from the LEDs toward the skin. To do this, the said light guide 5 is in the shape of a substantially circular plate in one piece, having a smooth outer surface which is a light projection surface 51. The light guide 5 also has an opposite face 52 which is arranged facing the said projection surface 51 and separated from the latter by a substantially cylindrical side wall 55. The LEDs are thus distributed around the light guide 5 opposite the side wall 55. The said opposite face 52 comprises distribution means 53 intended to distribute the light along the projection surface 51.

Figure 5:
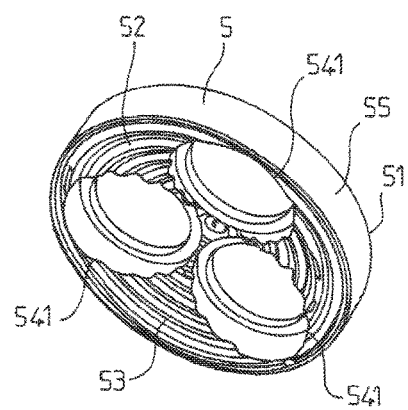
FIG. 5 is a perspective view of the light guide according to a first embodiment.

According to a first embodiment of the light guide 5, and as visible in FIG. 5, the distribution means 53 have a series of circular and concentric ridges inscribed on the opposite face 52 which is slightly concave or tapered inwardly. Through holes 541 allow the passage of the massage heads 31. The light guide 5 is rotated as a result of the movement of the heads. Other forms of distribution means may also be appropriate in order to guide the light, such as splines inscribed on the opposite face which is flat, concave, or tapered inwardly. The ridges and splines may also be combined to have a reflection effect in a broader perimeter.

Figure 7:
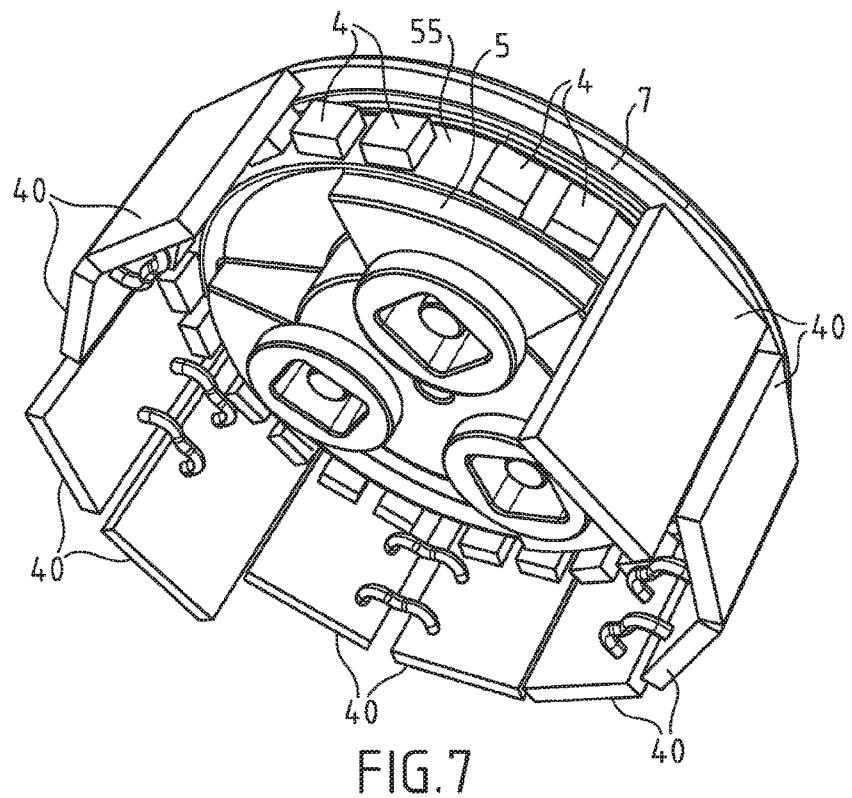
Figure 10:
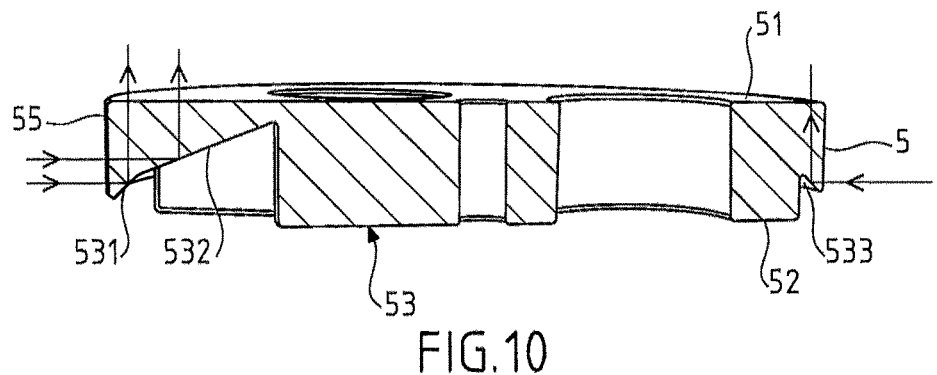
FIG. 10 is a sectional view of the light guide in the plane AA of FIG. 8 according to the second embodiment.

According to a second embodiment of the light guide 5, and as visible in FIGS. 7, 8 and 10, the distribution means 53 comprise peripheral slopes 531, 533 intended to reflect the light toward the periphery of the light guide 5. FIG. 10 illustrates a sectional view in the plane AA of FIG. 8 permitting visualization of the said peripheral slopes 531, 533. Three through holes 542 allow the passage of the massage heads. The distribution means 53 also comprise intermediate slopes 532 which contribute to the reflection of light toward an intermediate area of the guide, corresponding to an area between the periphery and the through holes 542; this area is illustrated in FIG. 8 with solid black. The fact that the light extends only to three angular portions permits optimizing the proportion of light reflected toward the center of the treatment area (ZT) and the portion left available for the massage heads. The larger the guide portions, the more the center is favored; the smaller they are, the more the massage heads are favored.

The light guide 5 is preferably made of polymethyl methacrylate (PMMA), a material that has a good medium index and thus good reflection at the interfaces, and has good transparency and thus little energy absorption. The optimization method is relatively simple and is based on the principle of total internal reflection. When light is injected into a material and reaches a surface, if the incidence is high enough, the totality of this light will be reflected and will thus be "trapped" by the material. The advantage of this reflection (as opposed to reflection on a metalized surface) is that it takes place without loss and may thus be repeated a great many times.

The LEDs 4 are arranged such that during projection in the light guide 5, the angle of incidence is greater than 42°, which is the limit for achieving maximum reflection in PMMA.

In order to improve the uniformity of the lighting, the use of an additional part which is a front window 6 above the light guide 5 may be envisioned. As visible in FIGS. 6 and 8, this part conforms to the shape of the light guide 5 in order to be pressed against it. A ring 7 permits holding everything in place. The said front window 6 is made of a specific material which is a polymethyl methacrylate (PMMA) to which small glass beads have been added. The small beads behave as water droplets in suspension in air, generating a mist. The material thus has a milky appearance due to the diffusion of light in the material. The front window 6 may also have a charmille surface finish for the lower and upper faces of the part. It is possible to make the assembly of the light guide 5 and the front window 6 using a bi-injection process.

Figure 6:
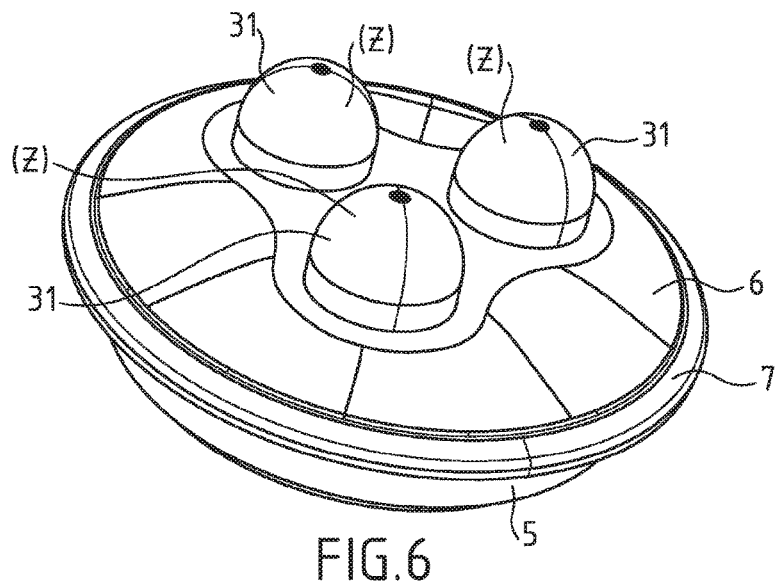

Concerning the massage means 31, they each have an area (Z) of contact with the skin to be massaged as visible in FIG. 6. An exploded view of a massage means 31 illustrated in FIG. 9 shows that the massage means or the massage head 31 has a hemispheric portion 36 which is connected to a cylindrical body 33. The massage head 31 further comprises a cover 32 that defines the said contact area and is above the portion 36. The said cover 32 is made of a thermoplastic elastomer (TPE) material permitting homogeneity of lighting. More specifically, the said material has a light transmission of between 0.8 and 0.9 for light with a wavelength of 590 nm or 630 nm.

The light transmission values may be measured using a spectrophotometer. The sample to be analyzed is then placed in this reference device during measurement.

In addition, the said material has a hardness of between 30 and 70 Shore A for a finish that is pleasant to the touch.

The material may be chosen from the family of hydrogenated styrene block copolymers (HSBC). Certain materials in the polyurethane (PU) or styrene-ethylene-butylene-styrene copolymers (ESBS) family may also be suitable.

It is preferable to choose a material that is appropriate for the treatment device described here, has good compatibility with the cosmetics that may be applied to the skin during the use of the device, and has good adhesion on polymethyl methacrylate (PMMA), the material of the part on which it is overmolded, such as the material TEFI 910 by MITSUBISHI CHEMICAL.

The said cover 32 is connected to the said portion 36 by overmolding. It is possible to make on the cover 32 a contact area having an unpolished surface finish with an arithmetic roughness Ra of about 0.5 µm to 1 µm in order to offset any lack of volume diffusion with surface diffusion.

Figure 11:
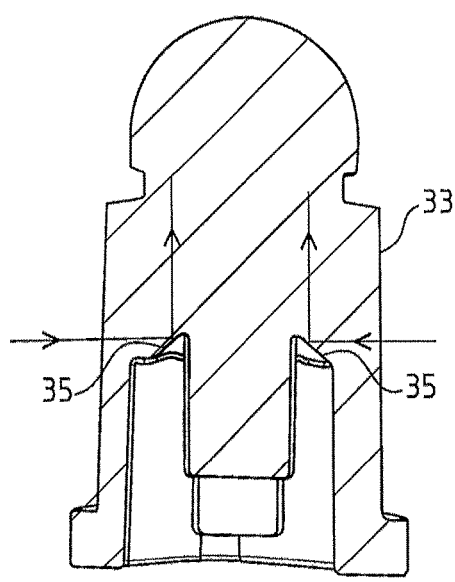
FIG. 11 is a sectional view in the plane BB of FIG. 9 of the massaging means.

To better light the treatment area (ZT), especially the places where there are massage heads 31, each massage head 31 comprises reflection means 35 in its interior in order to permit reflection of light toward the said contact area (Z). As illustrated in FIG. 11, which is a sectional view of the cylindrical body 33 in the plane BB of FIG. 9, the massage head has a tilted surface 35 opposite the lateral surface of the cylindrical body 33, which permits fully reflecting the light toward the top of the cylindrical body 33.

In order to conceal the interior of the light guide and make the projection of the light beam as homogeneous as possible, the projection surface 51 may be frosted or grainy, for example with a chemical or charmille graining.

Of course, the invention is in no way limited to the embodiments described and illustrated, which have been provided only as examples. Modifications are still possible, in particular from the point of view of composition of the various components or by substitution of equivalent techniques, without departing from the scope of protection of the invention.

The invention claimed is:

1. A skin treatment device comprising:
   a body comprising a housing forming a gripping area;
   electrical supply means arranged in the body;
   at least one treatment head comprising massage means;
   means for maneuvering the massage means actuated by an electric motor which is connected to the electrical supply means;
   at least one light source, and
   at least one light guide having a projection surface configured to receive light emitted by the at least one light source and to project at least one light beam toward an area on the skin,
   wherein the at least one light guide comprises a face opposite the projection surface, the opposite face of the at least one light guide comprising distribution means configured to distribute the light along the projection surface, and the massage means has an area for contact with the skin to be massaged, the area being configured to transmit the light and consisting of a thermoplastic elastomer material having a light transmission of between 0.8 and 0.9 for a light with a wavelength of 590 nanometer (nm) or 630 nm.

2. The skin treatment device according to claim 1, wherein the thermoplastic elastomer material has a hardness of between 30 and 70 Shore A.

3. The skin treatment device according to claim 1, wherein the contact area has an unpolished surface finish with an arithmetic roughness Ra of about 0.5 micrometer (µm) to 1 µm.

4. The skin treatment device according to claim 1, wherein the massage means comprise at least one massage head configured to be moved in rotation according to at least one vertical axis of rotation which is perpendicular to the projection surface.

5. The skin treatment device according to claim 4, wherein the at least one massage head has a hemispheric portion.

6. The skin treatment device according to claim 4, wherein the at least one massage head comprises a cover defining the contact area.

7. The skin treatment device according to claim 6, wherein the cover is fixed to the hemispheric portion by overmolding.

8. The skin treatment device according to claim 4, wherein the at least one massage head comprises reflection means permitting reflecting the light toward the contact area.

9. The skin treatment device according to claim 1, wherein the at least one light source comprises a plurality of light-emitting diodes distributed around the at least one light guide.

10. The skin treatment device according to claim 1, wherein the distribution means comprise at least one peripheral slope configured to reflect the light toward a periphery of the at least one light guide.

11. The skin treatment device according to claim 1, wherein the distribution means comprise at least one intermediate slope configured to reflect the light toward an intermediate area of the at least one light guide.

12. The skin treatment device according to claim 1, wherein the at least one treatment head is detachable from the body.

13. The skin treatment device according to claim 12, wherein the at least one treatment head comprises at least two different treatment heads interchangeable on the body.

\* \* \* \* \*